United States Patent [19]
Bock

[11] Patent Number: 5,369,831
[45] Date of Patent: Dec. 6, 1994

[54] THERAPEUTIC ULTRASONIC TOOTHBRUSH

[75] Inventor: Robert T. Bock, Brewster, N.Y.

[73] Assignee: Sonex International Corporation, Brewster, N.Y.

[21] Appl. No.: 84,979

[22] Filed: Jun. 25, 1993

Related U.S. Application Data

[63] Continuation-in-part of Ser. No. 911,489, Jul. 10, 1992, Pat. No. 5,247,716, and a continuation-in-part of Ser. No. 674,123, Mar. 25, 1991, Pat. No. 5,138,733.

[51] Int. Cl.$^5$ .................. A61C 17/20; A61C 17/22
[52] U.S. Cl. .................. 15/22.1; 15/167.1; 15/176.6; 433/119
[58] Field of Search .......... 15/22.1, 22.2, 167.1; 433/119, 118, 216

[56] References Cited

U.S. PATENT DOCUMENTS

| | | | |
|---|---|---|---|
| 1,703,642 | 2/1929 | Sticht | 15/22.1 |
| 1,963,389 | 6/1934 | Vardeman | 15/188 |
| 2,219,753 | 10/1940 | Sequin | 15/188 |
| 3,335,443 | 8/1967 | Parisi et al. | 15/22.1 |
| 3,375,820 | 4/1968 | Kuris et al. | 15/22.1 |
| 3,760,799 | 9/1973 | Crowson | 128/62 A |
| 3,809,977 | 5/1974 | Balamuth et al. | 15/22.1 |
| 3,879,139 | 4/1975 | Dahl et al. | 15/176.6 |
| 3,980,906 | 9/1976 | Kuris et al. | 15/22.1 |
| 4,192,035 | 3/1980 | Kuris | 15/22.1 |
| 4,333,197 | 6/1982 | Kuris | 15/22.1 |
| 4,372,296 | 2/1983 | Fahim . | |
| 4,646,725 | 3/1987 | Moasser . | |
| 4,698,058 | 10/1987 | Greenfeld et al. . | |
| 4,787,847 | 11/1988 | Martin et al. | 433/119 |
| 4,907,572 | 3/1990 | Borodulin et al. . | |
| 4,982,730 | 1/1991 | Lewis, Jr. . | |

FOREIGN PATENT DOCUMENTS

| | | | |
|---|---|---|---|
| 3431481 | 2/1986 | Germany | 433/118 |
| 556805 | 5/1977 | U.S.S.R. . | |
| 0506421 | 1/1978 | U.S.S.R. . | |
| 1066597A | 1/1984 | U.S.S.R. . | |

Primary Examiner—Edward L. Roberts
Attorney, Agent, or Firm—Watson, Cole, Grindle & Watson

[57] ABSTRACT

A removable brush-head for an ultrasonic toothbrush for daily dental hygiene purposes, including a plurality of bristle clusters, a substantially tubular body constructed of a flexible material and tensioning means securing the brush-head to the ultrasonic device, providing for the efficient transmission of ultrasonic frequency vibrations from the device via the brush-head to the teeth and gums and oral tissue of the user to loosen and remove soft plaque therefrom and to treat oral lesions.

3 Claims, 5 Drawing Sheets

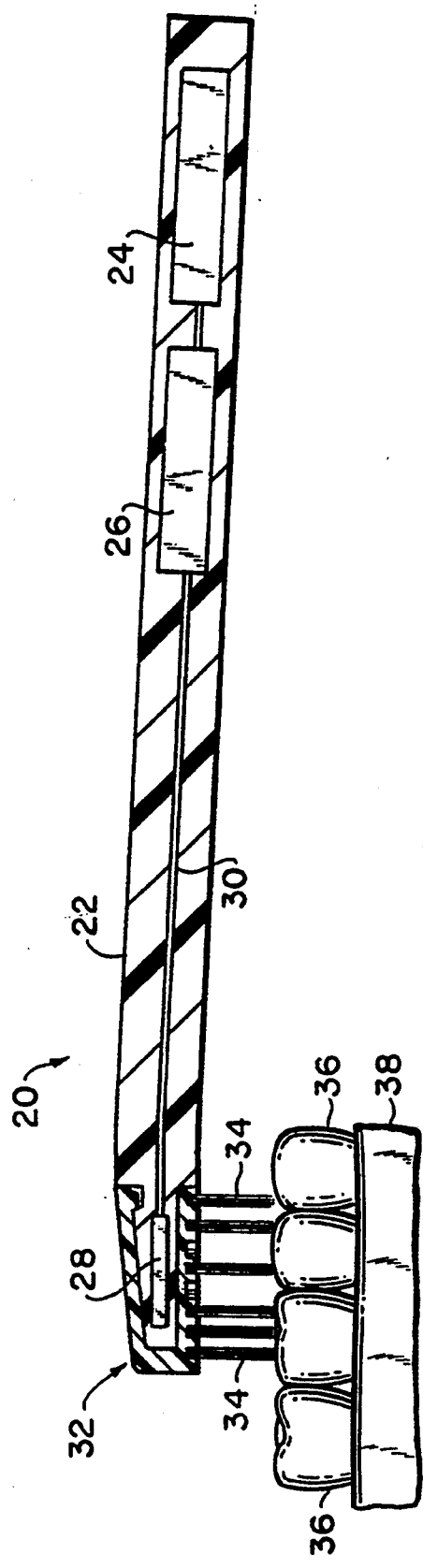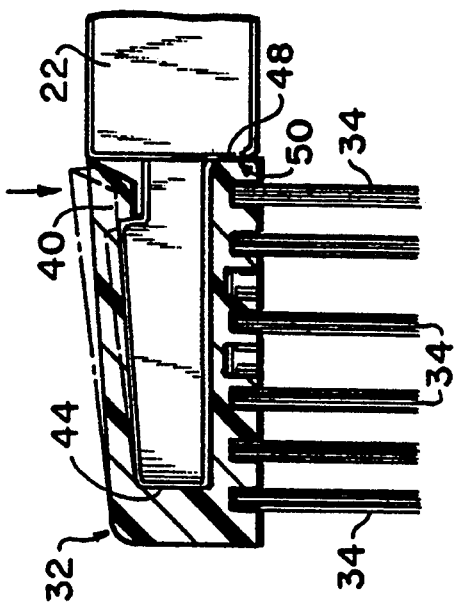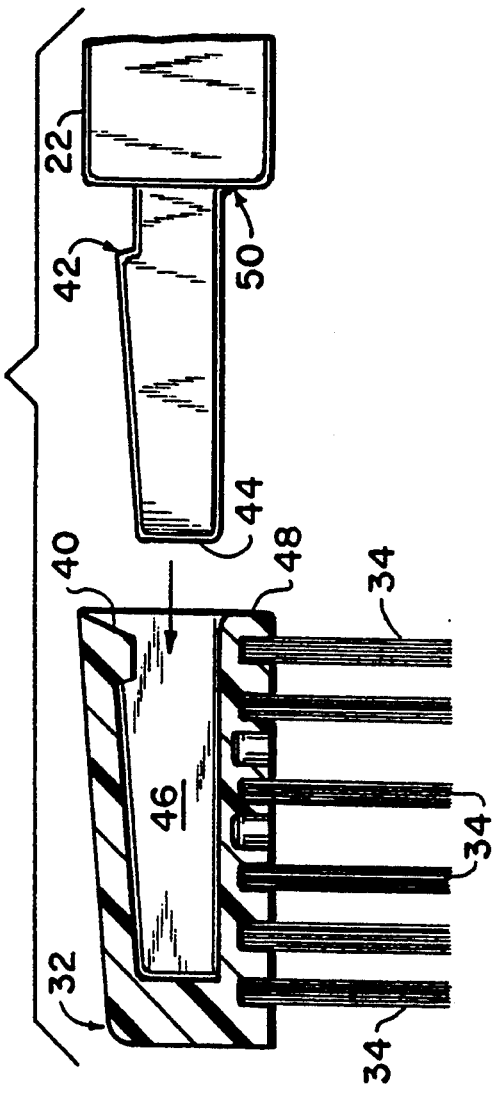

THERAPEUTIC ULTRASONIC TOOTHBRUSH

RELATED APPLICATION

This application is a continuation-in-part of U.S. patent application Ser. No. 07/911,489, filed Jul. 10, 1992 entitled "Removable Brush-Head for Ultrasonic Toothbrush, now U.S. Pat. No. 5,247,716; and U.S. Pat. No. 5,138,733, which issued May 18, 1992 from U.S. application Ser. No. 07/674,123, filed Mar. 25, 1991 entitled "Ultrasonic Toothbrush".

BACKGROUND OF THE INVENTION

This invention relates to toothbrushes. More particularly the invention is concerned with an apparatus facilitating the use of ultrasonic energy to assist an otherwise manual toothbrush in loosening and removing soft plaque from the teeth of the user on a substantially daily basis. A specific concern of the invention is an apparatus that carries the bristle clusters, which is readily replaceable as wear of the bristles occur. Another concern is the therapeutic treatment of oral tissue, and specifically treatment and prevention of mouth sores.

BACKGROUND—DESCRIPTION OF PRIOR ART

Numerous attempts have been made to develop an apparatus to remove plaque or tartar from the surface of the teeth. Some of the devices utilized sonic and/or ultrasonic energy. The devices utilizing sonic or ultrasonic energy can be grouped into three distinct categories.

One approach is the utilization of only fluids as a medium of energy transmission and plaque removal by placing an ultrasonic transducer into the middle of the mouth. This approach is impractical and physiologically dangerous due to the high energy levels it requires to be effective in absence of any mechanical scrubbing, and the uncontrolled, variable, user dependent distance between the transducer and the teeth. A typical example is U.S. Pat. No. 3,760,799.

The second approach is the application of ultrasonic energy to vibrate the toothbrush. While these teachings are aged, no application to date has demonstrated the practical feasibility of carrying out the science in this manner. The significant drawback of some of these proposals is that the toothbrush or applicator is solidly attached, otherwise fixed to the transducer, making replacement of the brush difficult and expensive, taking the device out of the economically affordable daily dental hygiene device category for the general population. Examples of these devices can be found in the following U.S. Pat. Nos.: 4,192,035, 4,333,197 and 4,787,847.

The third and only theory reduced to practice to date is to remove hardened or calcified plaque colonies from the surface of the teeth on infrequent periodical basis. This art has been made available to professional dentists in the form of a high energy device that couples the ultrasonic energy to the teeth by a metal probe. While safe in the hands of the highly skilled and professionally trained dentists or hygienists, these devices are not suitable for daily use by the general population. Such devices could case damage to the surface of the teeth and the surrounding tissue when utilized by un-trained novice consumers. What has occurred to date is that notwithstanding the teachings of the prior art, the ability to utilize ultrasonic energy to assist the consumer in the daily maintenance of oral hygiene in a safe and effective manner has remained unsolved.

In addition, the treatment of mouth sores in the oral cavity generally requires separate therapy which is time consuming and inconvenient. A combined cleaning and tissue therapy is thus desirable.

OBJECTS AND ADVANTAGES OF THE INVENTION

Responding to the above-described unsolved needs, this invention provides an ultrasonic toothbrush that is safe and effective to assist the consumer in the daily maintenance of oral hygiene. The invention attains this goal by positioning a piezoelectric transducer in the head section of an otherwise manual toothbrush. The piezoelectric crystal, resonating at or about its resonant frequency, emits ultrasonic waves between the bristles and couples the energy to the surface of the teeth via the dentifrice in the users mouth.

An object of the present invention is to provide a safe ultrasonic energy coupling mechanism to the user's teeth to dislodge and remove soft plaque.

Another object of the invention is to provide an effective cleaning device while reducing the ultrasonic energy level to the point where the daily application in the hands of an untrained novice will not harm the surface of the teeth or the surrounding soft tissue.

A further object is to provide an inexpensive removable brush component, independent from the sealed ultrasonic energy emitter, that can be easily replaced by the consumer. The brush component must provide for adequate interface between the surfaces of the main body containing the piezoelectric transducer, and the surfaces of the brush component, for efficient transmission of the ultrasonic energy.

Yet another object of the invention is to provide means for the daily cleaning of teeth which also allows for the treatment and prevention of mouth sores at the same time.

BRIEF DESCRIPTION OF THE DRAWINGS

In the accompanying drawings, in which certain modes of carrying out the present invention are shown for illustrative purposes:

FIG. 1 shows a longitudinal cross section of the invention in the replaceable brush-head configuration, including a battery powered driving circuitry.

FIGS. 2 and 3 show the lock-in attachment methodology of the brush-head to the handle of the ultrasonic device, in a cross sectional view.

DESCRIPTION OF THE PREFERRED EMBODIMENTS

Figure 4:
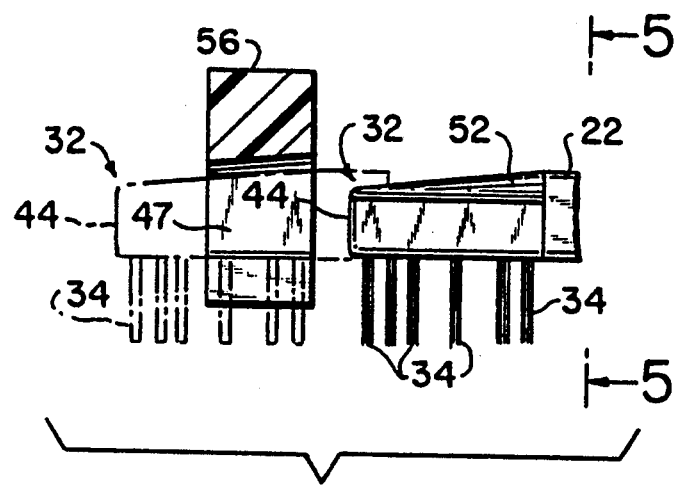
FIGS. 4, 5 and 6 show the brush-head unlocking tool and the removal methodology of the brush-head from the main body of the device.

Referring in detail to the drawings, the reference numerals herein refer to the like numbered parts in the drawings. In the following discussion, unless otherwise qualified, the term "ultrasonic" refers to either subsonic, sonic, or ultrasonic frequencies.

An ultrasonic toothbrush 20, in accordance with the present invention, is shown in FIG. 1. The toothbrush comprises of a handle 22 constructed of a rigid material, a battery pack 24, an electronics driving module 26, a piezoelectric transducer 28, connecting wiring 30, and a removable brush-head 32 made of a flexible material that encompasses a plurality of bristle clusters 34. The toothbrush is shown in a typical cleaning position, the bristle clusters 34 in contact with the teeth 36 in the oral cavity 38. The low voltage DC energy supplied by the battery pack 24 is converted to an ultrasonic frequency DC current by the electronics driving module 26, which is connected to the piezoelectric transducer 28 by the connecting wiring 30. The piezoelectric crystal resonates, expands and contracts volumetrically, in tune with the frequency supplied by the electronics driving module 26 and thereby converts the electronic energy into sound-wave energy. The sound-waves driving the dentifrices or other sonic medium in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 20 by the normal brushing movements of the user. The ultrasonic energy also beneficially affects adjacent lip, gum and facial tissue inside the oral cavity as hereafter noted.

The length of the bristle clusters 34 is selected to space the transducer 28 within an effective and controlled optimum distance to the teeth, allowing the reduction of the sound energy to biologically safe levels for routine daily application without causing harm to the surface or root structure of the teeth, and the surrounding soft tissue.

FIGS. 2 and 3 illustrate the lock-in attachment methodology of the brush-head 32 to the handle 22. The achieve a firm attachment, the brush-head 32 incorporates a tapered tongue section 40 and the handle incorporates a matching groove 42. To install a replacement brush-head 32, the user engages the rigid nose 44 section of the handle 22 with the flexible mouth 46 section of the brush-head 32. Upon engagement, the user forces the brush-head 32 upon the handle 22 until the movement is stopped by the lower mating surfaces 48 and 50 of the brush-head 32 and handle 22 respectively, and the tongue 40 snaps into the groove 42.

Figure 5:
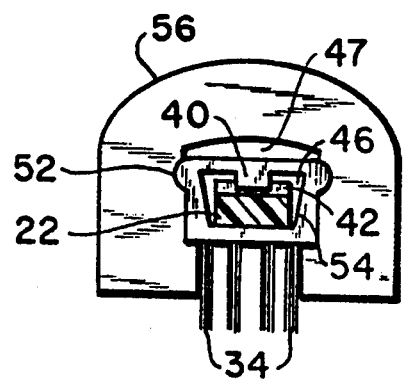
Figure 6:
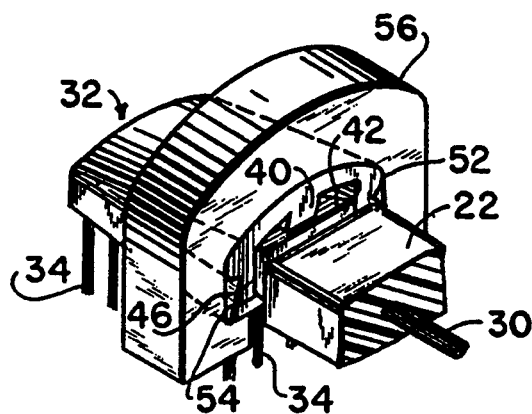

FIGS. 4, 5 and 6 illustrate the un-locking methodology of another configuration brush-head 32 from the handle 22. The brush-head 32 incorporates a tapered abutment 52 on each side that increases in size towards its mouth 46. The internal cavity of the mouth 46 is tapered 54, and increasing in size toward the abutments 52, forming a gap between the brush-head 32 and the handle 22 adjacent to the abutments 52. A removal tool 56 constructed of a material with superior strength and rigidity to the flexible brush-head 32 material, comprises a cavity that matches the lower and straight side dimensions of the brush-head 32 but larger than the brush-head 32 in the vertical dimension. As the user slides the rigid removal tool 56 upon the flexible brush-head 32, the sides with the abutments 52 of the brush-head 32 deform inwardly, causing the top section of the brush-head 32 with the tongue 40 to flex into the gap 47, out of the groove 42 of the handle 22, thereby unlocking the brush-head 32 from the handle 22.

FIGS. 6A–6E show an embodiment of the attachment and removal methodology of the brush-head to and from the handle of the device.

Figure 6A:
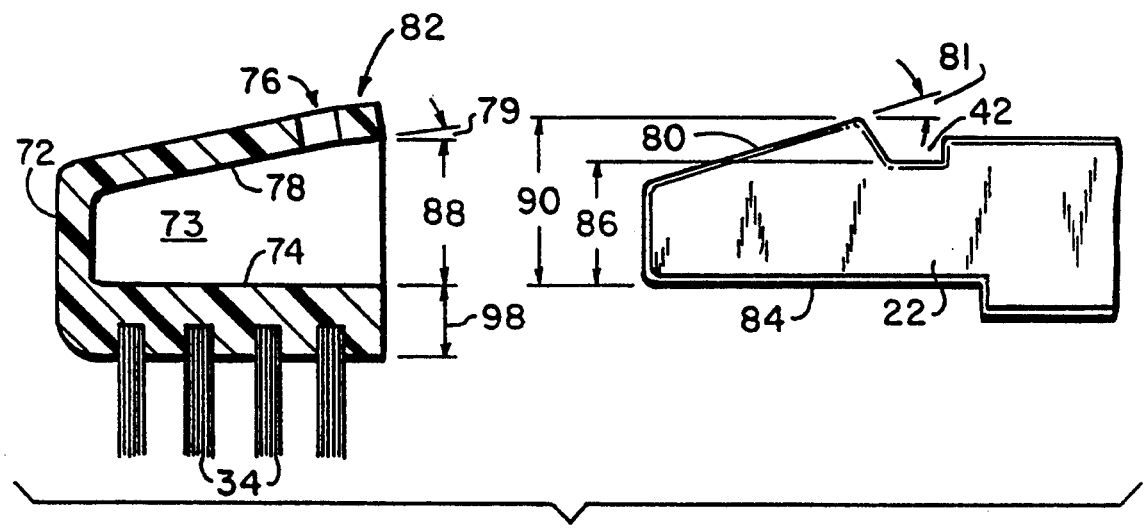
FIGS. 6A–6E show an embodiment of the attachment and removal methodology of the brush-head to and from the handle of the device.

FIG. 6A shows the preferred brush-head 72 constructed of a flexible material with varying wall thicknesses, incorporating a cavity 73 having a flat bottom surface 74 adjacent to the bristle clusters 34 and a tapered upper surface 78 opposite to the bristle clusters 34. The wall opposite to the bristle clusters 34 incorporates a slot 76 for the purpose of locking the brush-head 72 into place on the handle 22 and to secure it against accidental removal. The handle 22 constructed of a rigid material, incorporates a flat bottom surface 84 and a tapered upper surface 80, wherein the angle 81 of the tapered upper surface 80 is larger than the angle 79 of the tapered upper inside surface 78 of the brush-head 72 cavity 73. The handle 22 also comprises a groove 42 adapted to receive the flexible end portion 82 of the brush-head 72. The dimension 86 of the handle 22 is approximately the same as the dimension 88 of the brush-head 72, while the dimension 90 of the handle 22 is significantly larger than the dimension 88 of the brush-head 72.

Figure 6B:
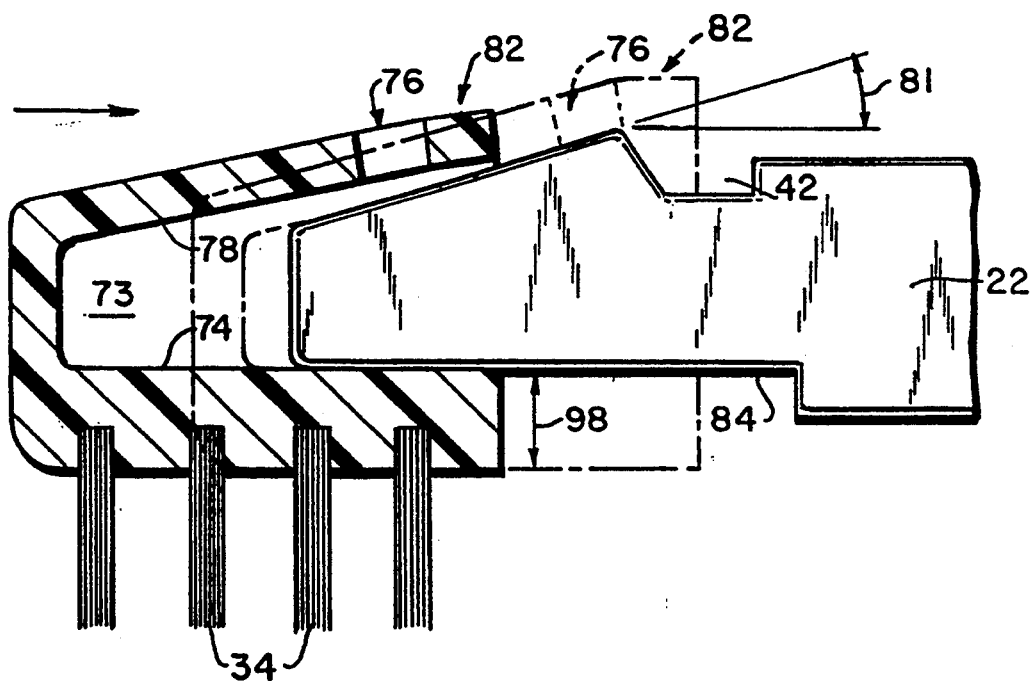

FIG. 6B shows the installation process of the brush-head 72 onto the handle 22. The user aligns the flat inside surface 74 of the brush-head 72 with the flat outer surface 84 of the handle 22, then proceeds to push the brush-head 72 onto the handle 22.

Figure 6C:
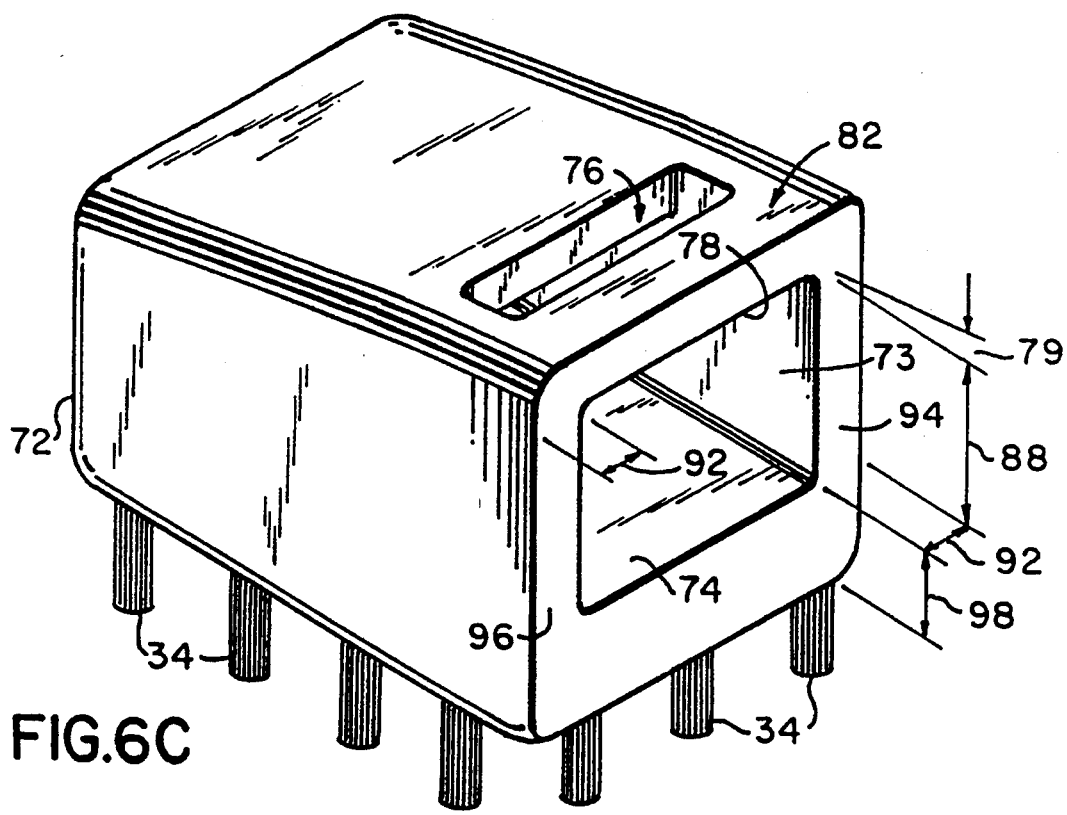
Figure 6C:
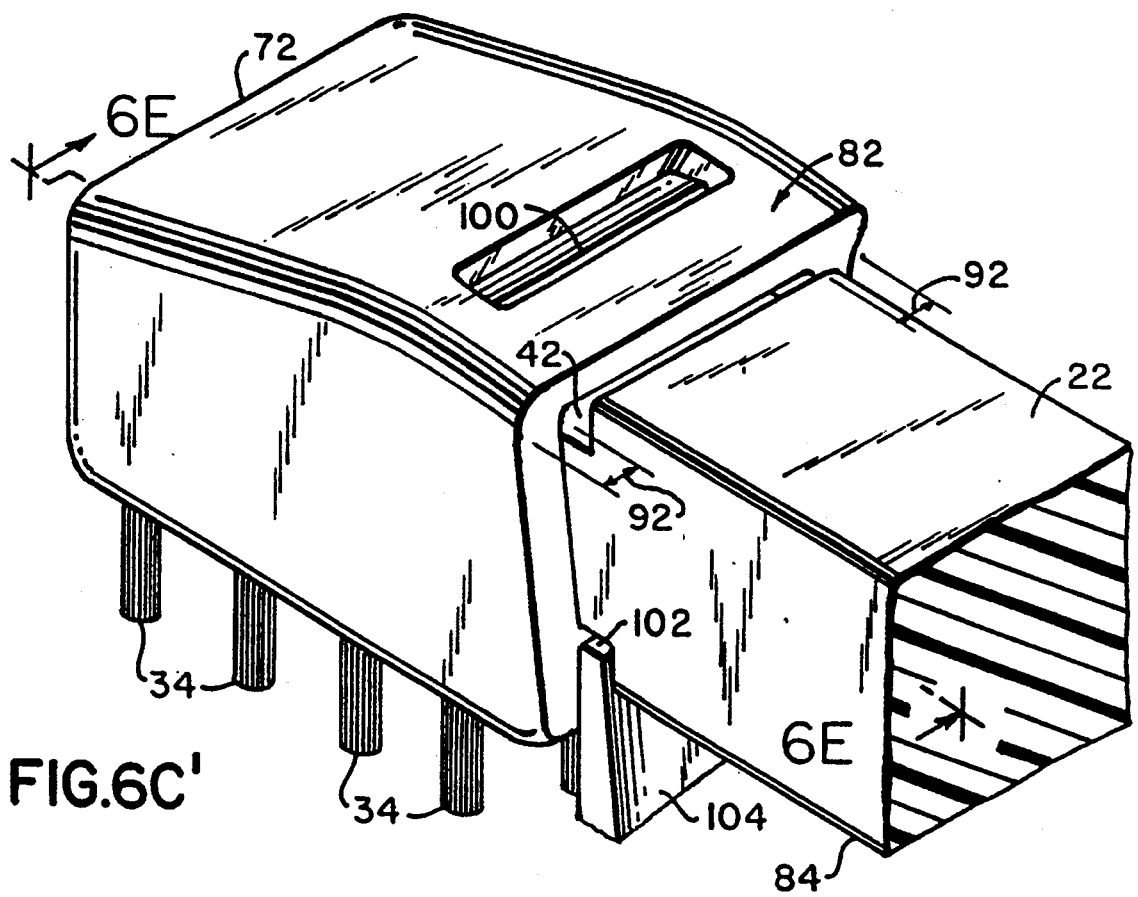

During the installation process, as shown in FIG. 6C and 6C', the larger angle 81 of the handle 22 expands the walls 94 and 96 of the brush-head 72 which is constructed with a smaller angle 79. The vertical wall thickness 92 of the brush-head 72 is designed to be substantially thinner than the bottom section 98 to assure that the expansion and the accompanying deformation of the brush-head 72 takes place within the side walls 94 and 96. The thickness of the bottom section 98 is calculated to assure that the inside flat surface 74 adjacent to the bristle clusters 34 of the brush-head 72 remains flat and not deformed by the expansion forces, and remains in intimate contact with the surface 84 of the handle 22.

Figure 6D:
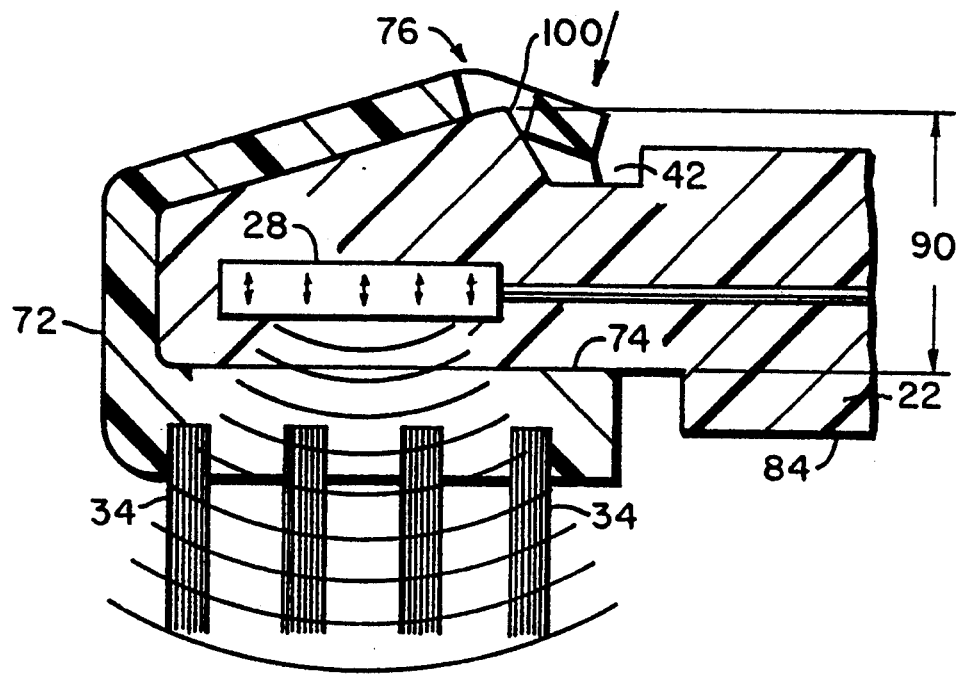

FIG. 6D describes the ultrasonic energy transmission methodology from the piezoelectric transducer 28 through the brush-head 72. When the brush-head 72 is pushed fully onto the handle 22, and the side walls 94 and 96 are expanded, the entire inside surface 74 of the brush-head 72 is forced into a tight and intimate contact with the outside surface 84 of the handle 22 by the tensional forces generated in the side walls 94 and 96 of the brush-head 72. This feature of matching surfaces in intimate contact is important for the efficient transmission of the ultrasonic energy from the piezoelectric crystal 28 through the handle 22 or the brush-head 72 and the bristle clusters 34. The volumetric expansion and contraction of the piezoelectric transducer 28 indicated by the double headed arrows generates the sound waves indicated by the curved lines, that are transmitted to the handle 22 and in turn to the brush-head 72 external surfaces and to the bristle clusters 34. The thickness 92 of the side walls 94 and 96 are also calculated to assure that the stress generated by the expansion force does not exceed the yield strength of the side walls 94 and 96. When designed in this manner, the stress generated in the side walls 94 and 96 will provide a force to maintain intimate contact between the surface 74 of the brush-head 72 and the surface 84 of the handle 22 throughout the life cycle of the brush-head 72.

Figure 6E:
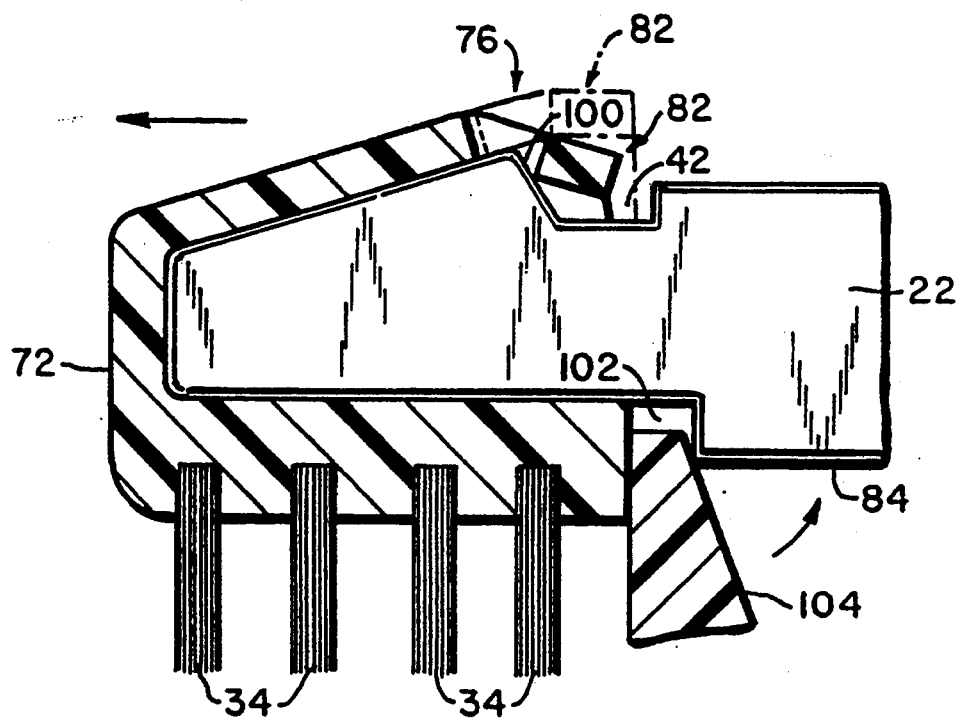

FIG. 6E shows the locking methodology of the brush-head 72 to the handle 22. As the end portion 82 of the brush-head 72 next to the slot 76 passes over the thickest dimension 90 of the handle 22, it is positioned directly above the groove 42 of the handle 22. The tensional forces in the side walls 94 and 96 pull the flexible end portion 82 of the brush-head 72 into the groove 42 of the handle 22, thereby locking the brush-head 72 into position on the handle 22. The angularity of the surface 100 is designed to prevent movement of the brush-head 72 by the forces generated of the bristle clusters 34 as they are rubbed against the teeth of the user, but to allow the removal of the brush-head 72 from the handle 22 when a significant axial pulling force is applied by the user.

FIG. 6E further shows the removal methodology of the brush-head 72 from the handle 22. The user presses a wedge 104 into a gap 102 formed between the brush-head 72 and the handle 22, perpendicular to the longitudinal axis of the handle 22. As the wedge penetrates, it widens the gap 102 and forces the brush-head 72 away from the handle in an axial motion, while the flexible end portion 82 of the brush-head 72 rides up on the angle 100 of the handle 22, releasing the brush-head 72. In practice, numerous other tools could replace the wedge 104 in the action of widening the gap. A screwdriver or a coin being twisted in the gap could fulfill the same function.

Figure 7:
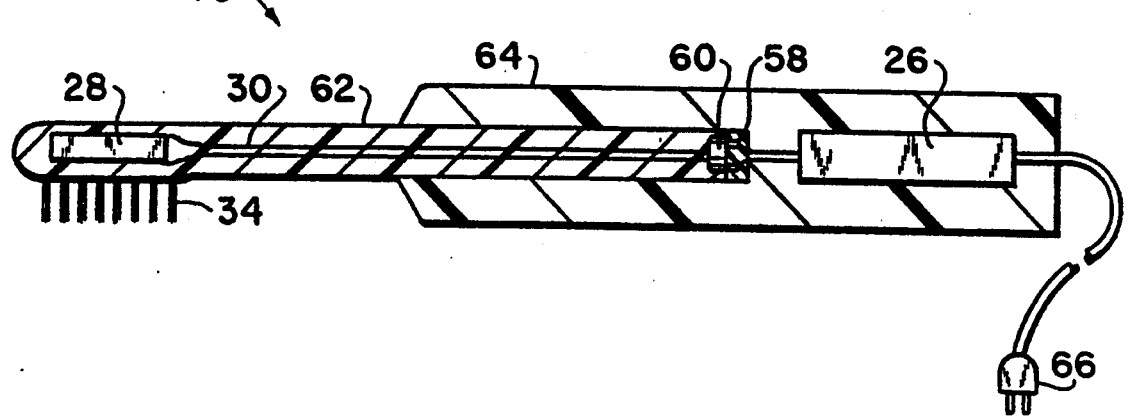
FIG. 7 shows an alternative embodiment of the invention where the replaceable brush element includes the piezoelectric crystal.

FIG. 7 shows an alternative embodiment of the invention, where the ultrasonic toothbrush 70 comprises of a AC line connector 66, a handle 64, an electronics module 26, a low voltage high frequency DC connector 58, and a replaceable brush element 62 that is further comprised of a plurality of bristle clusters 34, a piezoelectric transducer 28, connecting wiring 30, and another connector 60. The electronics module is energized by conventional AC house current through the line connector 66. The AC house current is converted to a low voltage, ultrasonic frequency DC current by the electronics module 26, which is connected to the piezoelectric transducer 28 by the connecting wiring 30 through the connectors 58 and 60. The piezoelectric crystal resonates, expands and contracts volumetrically, in tune with the frequency supplied by the electronics driving module 26 and thereby converts the electronic energy into sound-wave energy. The sound-waves driving the dentifrices in the mouth of the user against the teeth 36 causing mild cavitation within the dentifrices at the junction with the teeth, resulting in a loosening effect on the soft plaque on the surface of the teeth and in the periodontal pockets formed in the gums around the neck of the teeth. The loosened soft plaque is then dislodged by the bristle clusters 34 of the toothbrush 70 by the normal brushing movements of the user.

As can be seen readily in FIG. 1, the piezoelectric crystal 28 resonates, expands and contracts volumetrically, converting electronic energy into sound-wave energy. This energy is coupled to the bristles, and also to the entire volume of the brush-head 32. When the brush is used on a daily basis to clean teeth, the ultrasonic vibrations are also transferred to the tissues inside the oral cavity, in particular to the lips and facial tissues of the user through the back side of the brush head 32 as it rubs against the inside surfaces of the oral cavity. These ultrasonic vibrations have been shown to have therapeutic effects on recurrent aphthous stomatitis, commonly known as canker sores by reducing recurrence of the ulcers both in frequency and severity.

Thus, the invention achieved therapeutic action in the oral cavity when employed as a cleansing device.

CONCLUSION, RAMIFICATIONS AND SCOPE OF THE INVENTION

It can be seen that the invention provides a safe and effective ultrasonic toothbrush that can be utilized by any novice in the daily maintenance of oral hygiene. The fluid coupled ultrasonic energy, where metallic contact with the teeth has been eliminated, and the relatively low level but effective energy provides outstanding safety for both the teeth and the surrounding soft tissue. The reduced energy requirement is made possible by the controlled distance between the piezoelectric transducer and the teeth, that is established by the length of the bristle clusters. In particular, the removable toothbrush head allows for frequency replacement of the bristle clusters as appropriate. Finally, daily use of the device results in an effective treatment for mouth sores and a reduction in the severity and frequency of such mouth sores when they occur.

While the preceding description contain many specificities, these should not be construed as limitations on the scope of the invention, but rather as an exemplification of a preferred and additional embodiments thereof. Many other variations are possible. Skilled artisans will readily be able to change dimensions, shapes and construction materials of the various components described in the embodiments and adopt the invention to all types of sonic energy applications, from the subsonic range through sonic and to the ultrasonic range. Accordingly, the scope of the invention should be determined not by the embodiments illustrated, but by the appended claims and their legal equivalents.

What is claimed is:

1. A dental hygiene device for use with a dentifrice, comprising:
   a rigid elongated member of non-conductive material having a handle end and a bristle end;
   a piezoelectric transducer secured to the elongated member adjacent the bristle end for contracting and expanding volumetrically in response to a changing electrical field generating vibrations of ultrasonic frequency operative to cause mild cavitation in the dentifrice to loosen soft plaque on the surface of the teeth without appreciable relative movement of the bristle end with respect to the handle end, and to transmit ultrasonic vibrations to adjacent tissue;
   means coupled to the piezoelectric transducer operative for generating ultrasonic frequency electrical signals and transmitting said signals to said piezoelectric transducer;
   a plurality of bristle clusters for carrying dentifrice;
   means removably supporting the bristle clusters on the bristle end of the elongated member and being removably secured to the elongated member adjacent the piezoelectric transducer, said bristle clusters to be received within the human mouth for conducting said vibrations to the dentifrice and moved across tooth and gingival surfaces for dislodging the loosened soft plaque therefrom, and said means for supporting the bristle clusters having external surfaces adjacent said bristle clusters for contacting mouth tissue inside the oral cavity for reducing the recurrence and severity of mouth sores.

2. A dental hygiene device for use in the oral cavity with a sonic medium to clean teeth and to treat adjacent tissue comprising:

- an elongated substantially rigid handle member having opposite ends in spaced apart relation;
- a removable bristle support secured to the handle near one end thereof;
- a piezoelectric transducer secured within the handle adjacent the bristle support and responsive when energized for volumetrically contracting and expanding in response to a changing electrical field and generating vibrations of ultrasonic frequency in the sonic medium so as to cause mild cavitation in the dentifrice to loosen soft plaque on the surface of the teeth and the carry vibrations to adjacent tissue;
- means coupled to the piezoelectric transducer for generating ultrasonic frequency electrical signals and transmitting said signals thereto for energizing said piezoelectric transducer;
- a plurality of bristle clusters for engaging the teeth surfaces and being secured to the bristle support adjacent the piezoelectric transducer and extending transversely of the support for conducing the vibrations to the dentifrice and without appreciable relative movement between the bristle clusters and the handle and dislodging the loosened plaque from the teeth and to reduce the recurrence of various forms of ulcers and sores of the oral cavity both in frequency and severity by ultrasonic vibrations transmitted to said adjacent issue wherein the device is used as a dental hygiene device on a frequent basis.

3. The device of claim 2, wherein the bristle clusters extend laterally from the bristle support opposite the piezoelectric transducer to space said transducer from the teeth.

* * * * *